United States Patent [19]

Shim

[11] 4,278,085
[45] Jul. 14, 1981

[54] METHOD AND APPARATUS FOR METERED INFUSION OF FLUIDS

[75] Inventor: Norm Shim, Glenview, Ill.

[73] Assignee: Baxter Travenol Laboratories, Inc., Deerfield, Ill.

[21] Appl. No.: 103,041

[22] Filed: Dec. 13, 1979

[51] Int. Cl.³ .............................................. A61M 5/00
[52] U.S. Cl. ......................... 128/214 F; 128/DIG. 12; 417/477
[58] Field of Search ........... 128/214 R, 214 B, 214 E, 128/214 F, 214.2, 330, 273, DIG. 12, DIG. 13; 417/474–477, 441; 251/7, 8; 222/14–22

[56] References Cited

U.S. PATENT DOCUMENTS

| | | | |
|---|---|---|---|
| 2,366,424 | 1/1945 | Perry | 128/214 R |
| 2,393,838 | 1/1946 | Tarbox | 417/474 |
| 2,483,924 | 10/1949 | Moulinier | 128/214 F X |
| 3,620,650 | 11/1971 | Shaw | 417/476 X |
| 3,675,653 | 7/1972 | Crowley et al. | 128/278 |
| 3,726,613 | 4/1973 | Casimer | 417/477 |
| 3,731,680 | 5/1973 | Wright | 128/214 F |
| 3,990,444 | 11/1976 | Vial | 128/214 F |
| 4,155,362 | 5/1979 | Jess | 128/214 F |
| 4,210,138 | 7/1980 | Jess et al. | 128/214 F X |
| 4,217,993 | 8/1980 | Jess et al. | 128/214 E X |

FOREIGN PATENT DOCUMENTS

931304 7/1963 United Kingdom ................... 417/477

*Primary Examiner*—Stephen C. Pellegrino
*Attorney, Agent, or Firm*—Paul C. Flattery; John P. Kirby, Jr.; Eugene M. Cummings

[57] ABSTRACT

Metering apparatus for metering the flow of fluid through an administration set includes a peristaltic-type metering pump which repeatedly and progressively compresses a section of vinyl tubing of the administration set to provide a desired flow rate. For improved metering accuracy the fluid is maintained under pressure upline and downline of the metering pump to assist the tubing in becoming fully restored following each compression by the pump. In the illustrated embodiment, upline pressure is provided by a peristaltic-type pressure pump which is operated at a controlled rate to maintain a predetermined upline pressure, and downline pressure is provided by a spring-biased plunger which bears against the tubing downline of the metering pump to partially occlude the tubing.

52 Claims, 6 Drawing Figures

METHOD AND APPARATUS FOR METERED INFUSION OF FLUIDS

BACKGROUND OF THE INVENTION

The present invention relates to fluid infusion systems, and more particularly to an improved apparatus and method for accurately metering the flow rate of fluid through an administration set.

The infusion of fluids such as parenteral solutions and blood into the human body is usually accomplished by means of an administration set in conjunction with metering means for controlling the rate of fluid flow through the set. One form of metering means which is attractive for this application is the peristaltic-type pump, which operates to repeatedly and progressively compress and expand a section of tubing of the administration set so as to cause fluid to flow through the set at a controlled rate, thereby avoiding the need for direct contact with fluid and the attendant risk of contamination.

Because of its partial non-resiliency, tubing formed of vinyl and other thermal plastic materials commonly utilized in administration sets may permanently change its shape and size with time as a result of repeated stretch-compressive cycling, such as is inherent in the operation of a peristaltic-type pump, with the result that the rate at which fluid is delivered by the pump may undesirably vary with time. One means for minimizing the effects of stretch-compressive cycling for improved metering accuracy is described in U.S. Pat. No. 4,155,362, which issued to Thurman S. Jess on May 22, 1979, and is assigned to the present assignee. Basically this patent provides for flow restriction means downline of the peristaltic pump to obtain a downline fluid pressure at the point of compression by the pump which assists in restoring the tubing to its original shape following compression. This system has been successfully incorporated in the Model 2M8014 infusion pump manufactured by the Travenol Division of Baxter Travenol Laboratories, Inc., of Deerfield, Ill.

The present invention is directed to a peristaltic-type system and method for infusing fluids through vinyl tubing and the like which provides an additional improvement in metering accuracy by further minimizing physical dimensional variations in the tubing under repeated compression. Basically, this is accomplished by providing fluid pressurization means upline of the metering pump so that the fluid in the tubing segment upon which the metering pump is acting is pressurized both upline and downline of the point of engagement of the metering pump.

Accordingly, it is a general object of the present invention to provide a new and improved fluid infusion system.

It is a more specific object of the present invention to provide a new and improved system for infusing fluids into the human body with improved metering accuracy.

It is another object of the present invention to provide new and improved metering apparatus for controlling the flow of fluid through the compressible tubing of an administration set with improved metering accuracy.

It is another object of the present invention to provide a new and improved method for infusing fluid into the human body with greater metering accuracy.

SUMMARY OF THE INVENTION

The invention is directed to a flow system for infusing a fluid from a reservoir into a human body. The system includes a length of flexible-walled tubing extending from the supply reservoir to the body, this tubing being of the type which exhibits incomplete restoration upon repeated compressive cycling. Metering means continuously including at least one pressure means compressively engaged to the sidewall of the tubing are provided for completely occluding the lumen of the tubing. Drive means advance the point of engagement of the pressure means along a segment of the tubing, the lumen of the tubing being repetitively and progressively compressed and restored along the segment to urge fluid through the tubing. Downline pressurization means continuously at least partially restrict the lumen of the tubing downline of the tubing segment to increase the pressure of the fluid within the segment downline of the point of engagement. Upline pressurization means operatively engaged to the tubing increase the pressure of the fluid in the tubing segment upline of the point of engagement, the increase in pressure of the fluid at the point of engagement assisting in post-compressive reformation of the tubing for improved metering accuracy.

The invention is further directed to metering apparatus for infusing a fluid from a supply reservoir to the human body through a length of flexible-walled tubing of the type exhibiting incomplete restoration upon repeated compressive cycling thereof. The metering apparatus includes metering means continuously including at least one pressure means compressively engaged to the sidewall of the tubing for completely occluding the lumen of the tubing. Drive means are provided for advancing the point of engagement of the pressure means along a segment of the tubing, the lumen of the tubing being repetitively and progressively compressed and restored along the segment to urge fluid through the tubing. Downline pressurization means are provided for continuously at least partially restricting the lumen of the tubing downline of the tubing segment to increase the pressure of the fluid within the segment downline of the point of engagement. Upline pressurization means operatively engaged to the tubing are provided for increasing the pressure of the fluid in the segment upline of the point of engagement, the increase in pressure of the fluid at the point of engagement assisting in post-compressive reformation of the tubing for improved metering accuracy.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
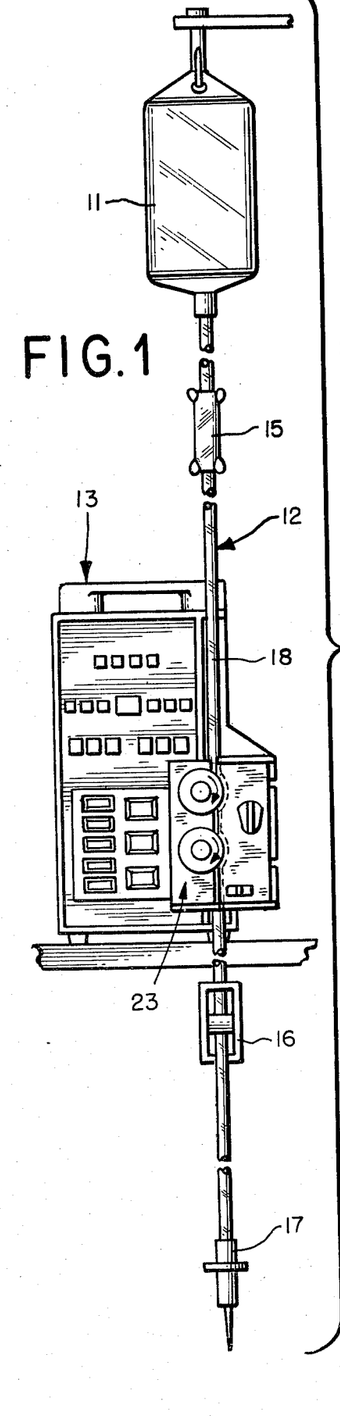
FIG. 1 is a front elevational view of an infusion system incorporating metering apparatus constructed in accordance with the invention.

Referring to the figures, and particularly to FIG. 1, an infusion system 10 constructed in accordance with the invention for injecting a fluid into a vein or artery of the human body from a reservoir 11 includes a disposable administration set 12 and a flow-controlling metering apparatus 13. The administration set, which may be conventional in design and construction, includes a drip chamber 15, a tubing clamp 16, a needle adapter 17, and a length of flexible transparent tubing 18 preferably formed of a thermo plastic material such as a vinyl. To avoid the danger of contamination, the administration set is packaged in a sterile and non-pyrogenic condition, and is disposed of after a single use.

Figure 2:
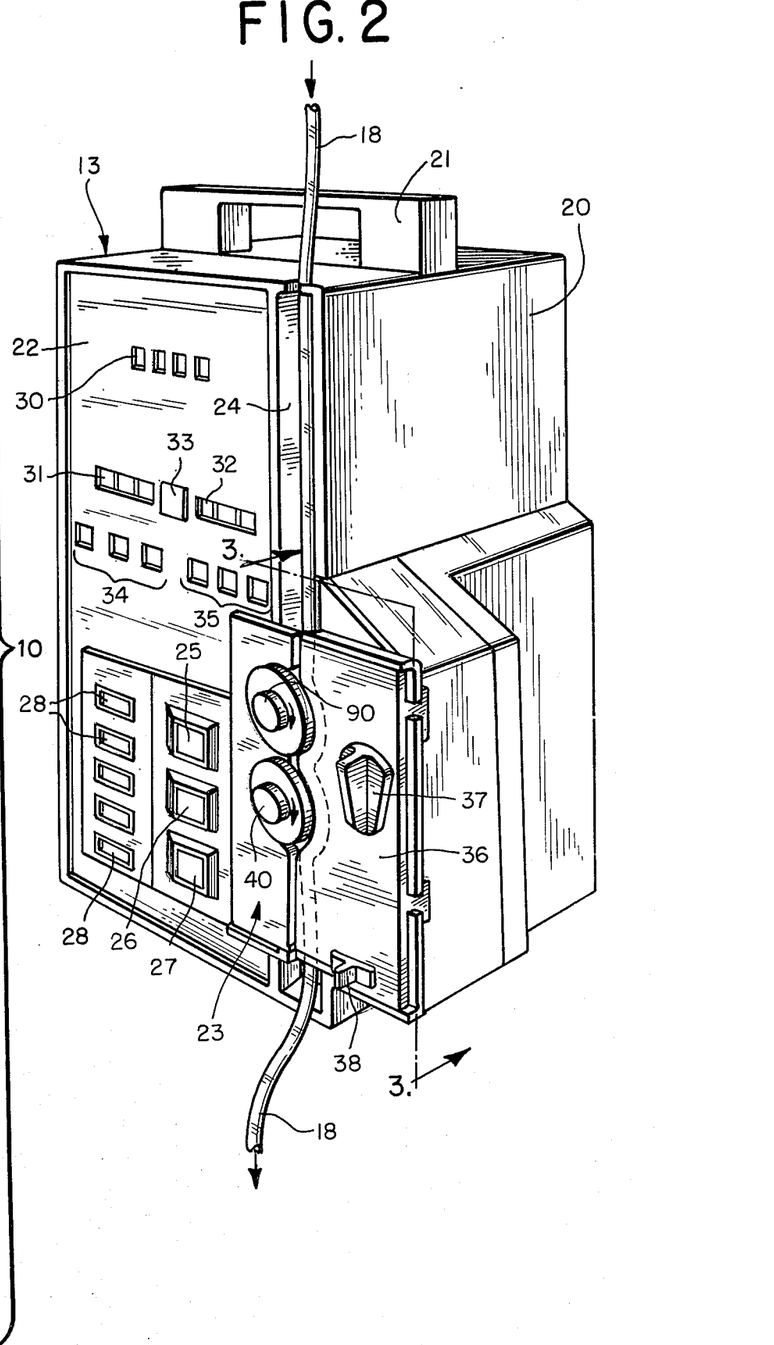
FIG. 2 is an enlarged perspective view of the metering apparatus shown in FIG. 1.

Metering apparatus 13, which is utilized in conjunction with administration set 12 for controlling the flow of fluid into a vein or artery, includes a generally rectangular housing 20 having a handle 21 at one end thereof for convenient carrying. Referring to FIG. 2, the front surface of housing 20 includes a control panel 22 which allows the operator to control and monitor the operation of the metering apparatus, and a peristaltic-type flow metering station 23 for compressing a section of tubing 18 to effect flow control of fluid in the administration set. A channel 24 is provided above the metering station for maintaining a portion of tubing segment 18 in a convenient position for viewing by the operator whereby flow irregularities can be more readily observed.

The operating mode of the metering apparatus is controlled by means of a push button STOP switch 25, a push button START switch 26, and a push button power ON-OFF switch 27. Each of these push button switches preferably includes an internal indicator lamp which provides a positive indication to the operator of the operating mode of the apparatus. Various abnormal operating conditions are annunciated by means of indicator lights 28 contained on control panel 22 to the left (as viewed in FIG. 2) of the mode control push buttons.

Control panel 22 further includes a digital display 30 of volume infused, a digital display 31 of volume to be infused, and a digital display 32 of fluid flow rate. The volume displayed by display 30 is the volume of fluid actually infused, and can be reset to zero by the operator by means of a push button RESET switch 33. The volume to be infused by display 31 is preset by the operator by means of a set of push button switches 34 to indicate a desired volume of fluid to be infused. Similarly, the infusion rate display 32 is preset by the operator by means of a second set of push button switches 35 to indicate the rate at which infusion is to take place.

The operation of the various indicators, control switches and other features of metering apparatus 13 is described in detail in the copending applications of Thurman S. Jess and Norm Shim, Ser. No. 856,863; Norm Shim, Ser. No. 857,018; Norm Shim and Vincent L. Knigge, Ser. No. 856,927; and Thurman S. Jess, Ser. No. 856,926; all filed Dec. 2, 1977.

The tubing 18 of administration set 12 passes through the flow control station 23 of metering apparatus 13. In accordance with conventional practice the flow control station 23 is provided with a slidably-mounted platen assembly 36 which may be opened by means of a control knob 37 to facilitate insertion or removal of the tubing. Further to this end, an additional control knob 38 is provided to allow user-displacement of a downline occlusion and safety element contained with the flow control station.

Figure 3:
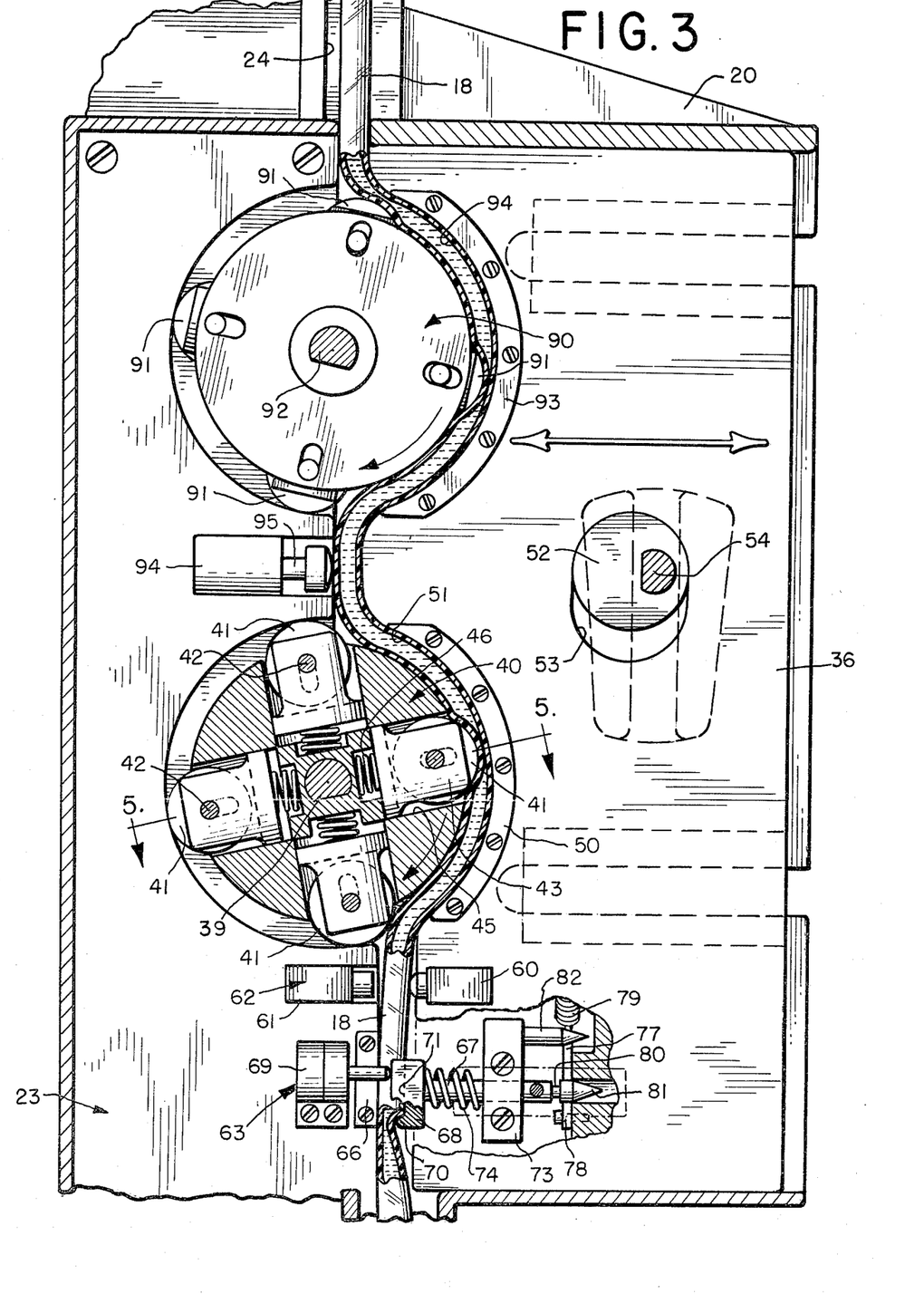
FIG. 3 is an enlarged front elevational view of the flow control station of the metering apparatus partially in section and partially broken away to illustrate the principal elements of the station.

Referring to FIG. 3, the fluid control station 23 includes metering means in the form of a rotor 40 mounted for rotation on a shaft 39 and having four pressure rollers 41 disposed in equi-spaced relationship about its circumference. The rollers are each mounted on a shaft 42 for free rotation, and the shaft are carried on individual carriages 43 mounted on the rotor for reciprocation within a radial recess 45. The carriages are each spring-biased in a radially outward direction by helical springs 46 disposed within the recesses.

The flow control station further includes a pressure plate 50 which provides an arcuate working surface 51 which substantially corresponds in shape to the circumference of rotor 40 and is positioned to bring a segment of tubing 18 into compressive engagement with rollers 41 around at least a portion of the rotor circumference corresponding to the distance between adjacent rollers. The pressure plate may be reciprocated toward and away from rotor 40 to facilitate installation and removal of tubing 18 by rotation of an eccentric cam, 52, which is constrained to movement within a vertical slot 53 provided on the pressure plate. Rotation of the cam is accomplished by a shaft 54 which connects with knob 37. When knob 37 is in its bottom position, as shown in FIG. 3, the pressure plate is moved sufficiently close to the rotor circumference to cause tubing 18 to be completely occluded by the rollers.

After passing through the peristaltic pump arrangement provided by rotor 40 and pressure plate 50, tubing 18 extends between a light source 60 and a photodetector 61, which together comprise a bubble detector station 62 for detecting the presence of bubbles in the flow system. The tubing then passes through downline pressurization means in the form of a flow restriction station 63. This station includes a slidably-mounted plunger 67 which is biased against the sidewall of tubing segment 18. The end of plunger 67 which engages the tubing segment includes a generally L-shaped head portion 68 having a wedge-shaped working surface 70 which occludes the tubing and a generally flat control surface 71 on which the fluid acts. The central body portion of the plunger is slidably received within a stationary mounting block 73, are extends through the center of a helical compression spring 74 which biases head 68 into engagement with the tubing.

Plunger 67 may be opened to facilitate loading or unloading of tubing segment 18 by means of the user-actuated knob 38 on the front panel. Automatic release of the plunger is obtained by means of a latch member 77 which is pivotally mounted at 78 to platen assembly 36 and biased by a helical spring 79 for operation within a plane perpendicular to the plunger. The plunger includes a slot 80 in which the latch member 77 is received when the plunger is moved to its full open position. The end 81 of the plunger is tapered to facilitate displacement of the latch member prior to seating in slot 80. Once the latch member has been received in the slot, the plunger is locked open and tubing 18 can be readily removed.

To insure that the plunger will be released when platen assembly 36 is subsequently closed, mounting block 73 is provided with an actuator pin 82 having a tapered end surface which serves to displace the pivotally mounted latch member 77 from slot 80 when the pressure plate is returned to its closed position by rotation of knob 37. In this way, the plunger is automatically released so as to again become spring-biased against the administration set tubing 18 as the metering station is closed. This prevents inadvertent operation of the system without the back pressure and gravity flow protection provided by the plunger.

Figure 5:
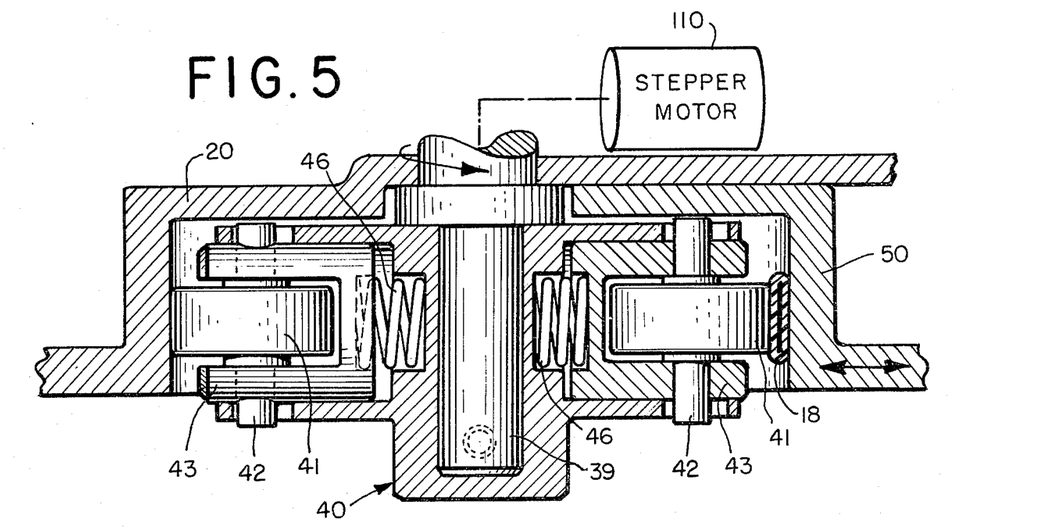
FIG. 5 is an enlarged cross-sectional view of the metering rotor assembly of the flow control station taken along line 5—5 of FIG. 3.

In operation, rotor assembly 40 is rotated clockwise (as viewed in FIG. 3) so as to bring pressure rollers 41 into compressive engagement with tubing 18 against pressure plate 50. As shown in FIG. 5, the force exerted on the tubing by rollers 41 is sufficient to completely occlude the tubing so that as the rotor assembly rotates liquid within the lumen of the tubing is forced to advance. By accurately controlling the speed of rotation of the rotor assembly, it is possible to accurately control the flow rate of fluid through the tubing.

Flow restriction stage 63, by partially occluding the tubing, increases the fluid pressure in the lumen of the tubing downline of the point of engagement of the pressure rollers. This pressure assists in expanding the walls of the tubing prior to and following compression by the pressure rollers to their uncompressed shape to minimize variations in the volume of fluid urged forward with each rotation of rotor 40. This feature of the metering apparatus is described in detail in the aforementioned U.S. Pat. No. 4,155,362.

In accordance with the invention, a further improvement in metering accuracy is achieved by providing in metering apparatus 13 upline pressurization means for increasing fluid pressure upline of the point of engagement of the pressure rollers. This has the effect of assisting in restoration of the tubing sidewall above the point of engagement and thereby achieves a further improvement in metering accuracy. Referring again to FIG. 3, in the illustrated embodiment upline pressurization means in the form of a second or additional rotor 90 is provided. This rotor is mounted for rotation on a drive shaft 92, and includes four pressure rollers 91 equispaced about its circumference. Pressure rollers 91 may be mounted for radial reciprocation relative to the rotor in the same manner as pressure rollers 41. A second pressure plate 93 having an arcuate working surface 94 corresponding generally to the circumference of rotor 90 is mounted on platen assembly 36 so as to bring tubing 18 into successive compressive engagement with pressure rollers 91 as rotor 90 rotates. Thus, rotor 90 and pressure plate 93 together form a peristaltic-type pump for pressurizing fluid in tubing 18 upline of the point of engagement of pressure rollers 41.

To insure that a desired upline pressure level will be maintained, metering apparatus 13 may include a pressure control system which responds to the upline pressure level in the tubing and adjusts the rate of rotation of rotor 90 to maintain a desired upline pressure level. To this end, the control system may include a pressure sensor 94 disposed in operative engagement with tubing 18 between the upline pressurization and metering means. Pressure sensor 94, which may be conventional in design and construction, may include a spring-biased plunger 95 which bears against the sidewall of the tubing such that the position of the plunger is indicative of the pressure level in the tubing. In a manner well known to the art, this position is converted to an electrical pressure-indicative signal which may be utilized by the apparatus control system to maintain the speed of rotation of rotor 90 at the speed required to maintain a desired upline pressure level.

One means for driving motor 90 is to provide a mechanical linkage with rotor 40. Then, as rotor 40 is driven at the required rotational speed by appropriate means, such as a stepper motor, the upline pressurizing rotor 90 would also be rotated to provide the required upline pressurization. With this arrangement, a clutching element responsive to the output of the pressure regulating circuit would preferably be provided in the mechanical linkage between the two rotors to enable the upline pressure to be more accurately controlled.

Figure 4:
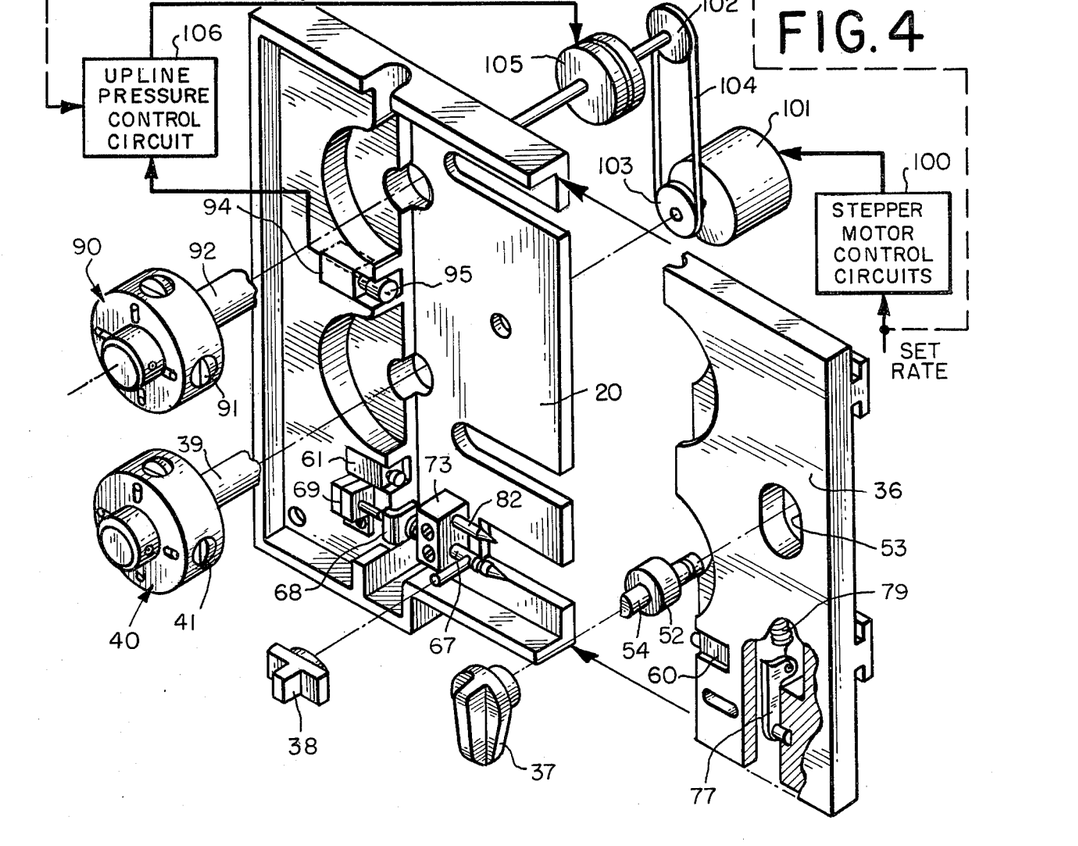
FIG. 4 is an enlarged exploded perspective view of the principal mechanical elements of the metering station shown in FIG. 3.

Referring to FIG. 4, in one possible form of mechanical coupling arrangement wherein rotor 40 is driven by motor control circuits 100 and a stepper motor 101, shafts 39 and 92 of the rotors are coupled by a mechanical linkage consisting of first and second drive pulleys 102 and 103 and an interconnecting drive belt 104. Pulley 102 is rotatably coupled to drive shaft 92 by means of an electrically-activated clutch 105. The output of pressure sensor 94, a signal indicative of the pressure level upline of the metering rotor assembly, is applied to an upline pressure control circuit 106. In this control circuit the sensed pressure is compared with a desired predetermined pressure level, and an appropriate control signal is generated for application to clutch assembly 105.

Optionally, should it be desired to maintain a different predetermined upline pressure level for different infusion rates, i.e., for different rotational speeds of rotor 40, the rate setting signal applied to stepper motor control circuits 100 may also be applied to upline pressure control circuit 106 to modify the predetermined pressure level established by the control circuit. Thus, for a higher infusion rate it would be possible to maintain a higher predetermined upline pressure level.

It will be appreciated that although a belt and pulley coupling arrangement is shown, it would be possible to use other mechanical coupling arrangements such as a gear train, to obtain rotational coupling between the rotors. Furthermore, various coupling ratios could be employed to optimize or limit the amount of declutching required of clutch assembly 105.

Figure 6:
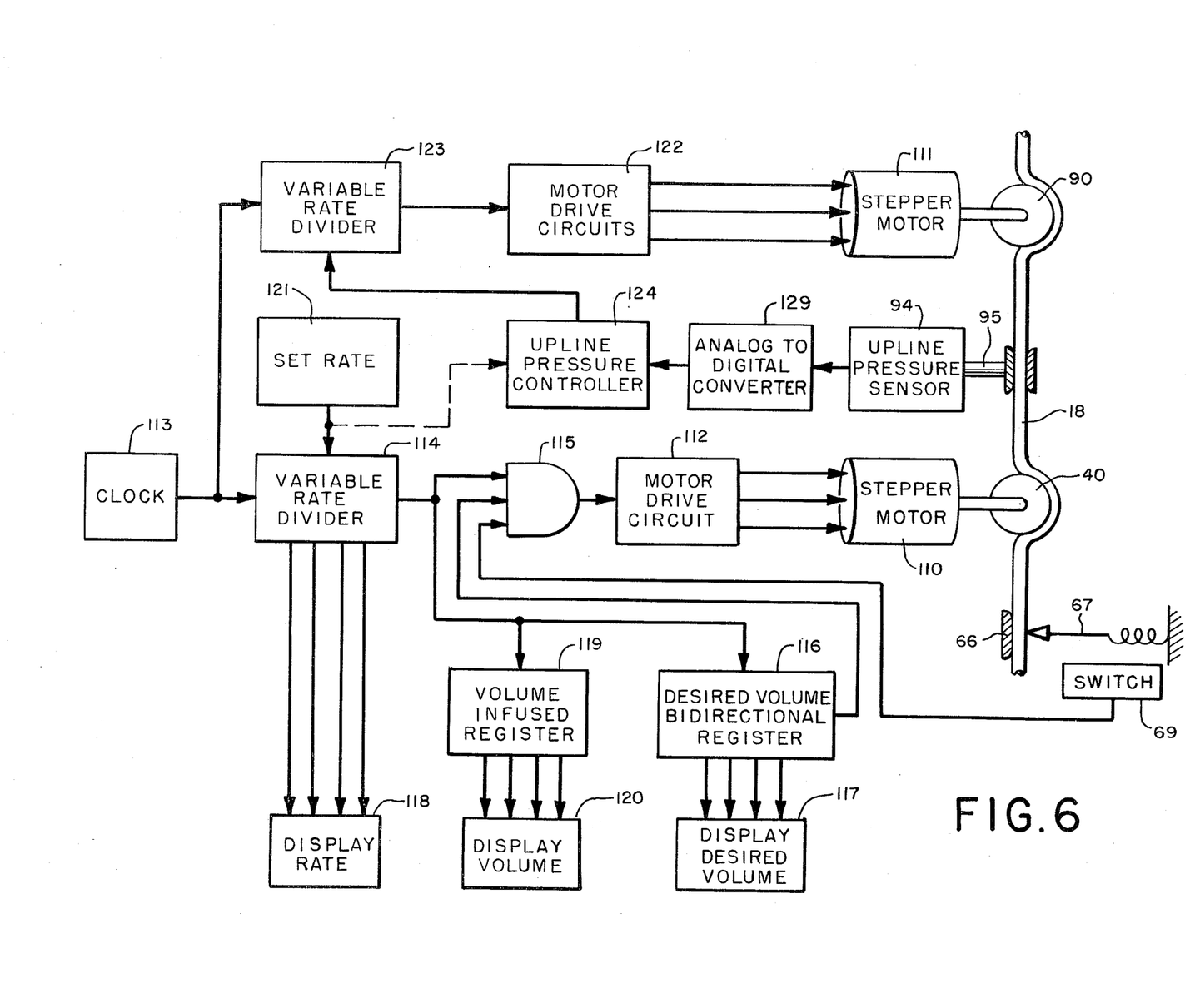
FIG. 6 is a simplified functional block diagram of the control system for the metering apparatus.

Greater flexibility in upline pressure control is possible utilizing individual stepper motors for driving rotors 40 and 90. On such system, wherein individual stepper motors 110 and 111 are provided for driving rotors 40 and 90, is shown in FIG. 6. The operation of the stepper motors is controlled by a clock 113. Pulses from the clock are applied to a variable rate divider 114, wherein a predetermined division factor is applied to obtain control pulses at a suitable rate for controlling stepper motor 110. The divided pulses are applied through an AND gate 115 to conventional motor drive circuits 112. The AND gate responds to an applied inhibit signal to interrupt application of control pulses to the drive circuit when a desired volume of fluid has been infused.

To provide an inhibit signal upon the desired volume being infused, the system includes a bi-directional register 116, which is initially set to the volume to be infused, and is then counted down to zero by pulses from divider 114. A display of the volume remaining to be infused is provided by a display circuit 117 associated with the bi-directional register. The application of control pulses to motor drive circuit 112 may also be interrupted by the actuation of a safety switch 69 upon plunger 67 being forced fully open, as may occur as a result of a downline blockage of tubing 18.

In the absence of inhibiting signals from bi-directional register 116 and safety switch 69, the divided pulses from variable rate divider 114 are applied to motor drive circuit 112 to cause stepper motor 110 to rotate one increment for each applied pulse. Thus, each pulse produces one increment of rotation, and precise flow control is achieved.

The infusion rate may be displayed by means of a display circuit 118 coupled to the variable rate divider 114. The volume infused may be indicated by applying the divided pulse from variable rate divider 114 to a volume infused register 119, and displaying the counting state of this register in an appropriate volume display circuit 120. The division factor of the variable rate divider 114 is set by means of a set rate circuit 121. This circuit may include user-actuable switching means for setting a desired infusion rate, and from this user input circuit 121 applies an appropriate control signal to rate divider 114.

The upline pressurization stepper motor 111 is driven by a motor drive circuit 122, which like drive circuit 112 may be conventional in design and construction. Drive circuit 122 is controlled by control pulses derived from clock 113 through a variable rate divider 123. The rate of rotation of stepper motor 111 is dependent on the repetition rate of the applied drive pulses, so that by varying the division factor of rate divider 123 it is possible to vary the rotational speed of rotor 90. To this end, the control system of metering apparatus 13 includes an upline pressure controller circuit 124 which receives the pressure-indicative output signal of upline pressure sensor 94 through an analog to digital converter 129 and generates an appropriate control signal for application to rate divider 123. When the pressure sensed by pressure sensor 94 falls below a desired predetermined level, pressure controller circuit 124 reduces the division factor of rate divider 123, thereby causing stepper motor 111 to increase speed and provided increased pressure in the upline segment of tubing 18. Conversely, when the pressure sensed by the pressure sensor 94 exceeds the desired predetermined level, the division factor of rate divider 123 is increased, causing fewer pulses to be applied to stepper motor 111 and the upline pressure to decrease. In this way, a closed-loop feedback circuit is formed which maintains a constant upline pressure level in tubing 18.

Optionally, the pressure level maintained in tubing 18 may be varied as a function of the operating rate of the metering apparatus. Specifically, the rate-indicative output signal developed by set rate circuit 121 may also be applied to the upline pressure controller circuit 124 to modify the desired pressure level maintained by that circuit. Then, the previously described feedback loop through rate divider 123 and drive circuit 122 functions to maintain the modified pressure level.

It is contemplated that for various types of infused fluids and various types of vinyl tubing, various upline pressures will be found to provide optimum metering accuracy. To this end, upline pressure control circuit 124 may receive additional inputs, such as tubing size and type fluid characteristics, and may include appropriate processing circuitry, such as a microprocessor, for deriving an optimum stepping rate for stepper motor 111 for a particular infusion application.

While rotary peristaltic-type pumps have been shown for the metering and upline pressurization means of the apparatus, it will be appreciated that other types of pumps, such as linear-type peristaltic pumps, may be employed instead. Furthermore, while the use of mechanical linkages and stepper motors has been shown as the upline pressurization means, it will be appreciated that other drive arrangements, such as direct current motors, may be used with appropriate modification of the control circuitry.

While particular embodiments of the invention have been shown and described, it will be obvious to those skilled in the art that changes and modifications may be made without departing from the invention in its broader aspects, and, therefore, the aim in the appended claims is to cover all sectional changes and modifications as fall within the true spirit and scope of the invention.

I claim:

1. In a flow system for infusing a fluid from a supply reservoir into the human body, having, in combination:
   a length of flexible-walled tubing extending from the supply reservoir to the body, said tubing exhibiting incomplete restoration upon repeated compressive cycling thereof;
   metering means continuously including at least one pressure means compressively engaged to the sidewall of said tubing for completely occluding the lumen thereof;
   drive means for advancing the point of engagement of said pressure means along a segment of said tubing, the lumen of said tubing being repetitively and progressively compressed and restored along said segment to urge fluid through said tubing;
   downline pressurization means for continuously at least partially restricting the lumen of said tubing downline of said tubing segment to increase the pressure of the fluid within said segment downline of said point of engagement; the improvement comprising:
   upline pressurization means operatively engaging said tubing for increasing the pressure of said fluid in said segment upline of said point of engagement, the increase in pressure of said fluid at said point of engagement assisting in post-compressive reformation of said tubing for improved metering accuracy.

2. A flow system as defined in claim 1 including pressure control means responsive to the pressure in said tubing upline of said point of engagement for varying the operation of said upline pressurization means to maintain said upline pressures at a predetermined level.

3. A flow system as defined in claim 2 wherein said pressure control means are also responsive to the rate of advance of said pressure means along said tubing segment.

4. A flow system as defined in claim 3 wherein said drive means advance said pressure means to maintain a predetermined fluid flow rate through said tubing, and wherein said predetermined upline pressure maintained by said upline pressurization means varies as a function of said predetermined rate.

5. A flow system as defined in claim 1 wherein said upline pressurization means comprise additional pressure means compressively engaged to the sidewall of said tubing for at least partially occluding the lumen thereof, and additional drive means for advancing the point of engagement of said additional pressure means along an additional segment of said tubing.

6. A flow system as defined in claim 5 including pressure control means responsive to the pressure of said fluid in said tubing between said pressure means and said additional pressure means to maintain a predetermined pressure in said tubing.

7. A flow system as defined in claim 6 wherein said pressure control means vary the rate of advance of said additional pressure means along said additional segment.

8. A flow system as defined in claim 6 including pressure sensing means disposed along said tubing between said segment and said additional segment for providing a control signal indicative of the fluid pressure level in said tubing between said pressure means and said additional pressure means, said additional drive means being responsive to said control signal to vary the drive of said additional pressure means to maintain a predetermined pressure level at said sensing means.

9. A flow system as defined in claim 8 wherein said control signal is applied to said additional drive means to vary the rate of advance of said additional pressure means along said additional segment.

10. A flow system as defined in claim 1 wherein said tubing is formed of vinyl.

11. A flow system as defined in claim 1 wherein said downline pressurization means comprise a slidably-mounted plunger spring-biased against the sidewall of said tubing.

12. In a flow system for infusing a fluid from a supply reservoir into the human body, having, in combination:
a length of flexible-walled tubing extending from the supply reservoir to the body, said tubing exhibiting incomplete restoration upon repeated compressive cycling thereof;
metering means including a rotor having along its circumference a plurality of pressure members, at all times at least one of said pressure members being in compressive engagement with the sidewall of said tubing and completely occluding the lumen thereof;
means including a pressure plate for bringing said tubing into compressive engagement with said one of said pressure members;
drive means for rotatably driving said rotor whereby the lumen of said tubing is repetitively and progressively compressed and restored along said segment to urge fluid through said tubing;
downline pressurization means for continuously at least partially restricting the lumen of said tubing downline of said tubing segment to increase the pressure of the fluid within said segment downline of said point of engagement of said pressure member; the improvement comprising:
upline pressurization means operatively engaging said tubing for increasing the pressure of said fluid in said segment upline of said point of engagement, said increase in pressure of said fluid at said point of engagement assisting in post-compressive reformation of said tubing for improved metering accuracy.

13. A flow system as defined in claim 12 including pressure control means responsive to the pressure in said tubing upline of said point of engagement for varying the operation of said upline pressurization means to maintain said upline pressures at a predetermined level.

14. A flow system as defined in claim 13 wherein said pressure control means are also responsive to the rate of advance of said pressure means along said tubing segment.

15. A flow system as defined in claim 14 wherein said drive means rotate said rotor to maintain a predetermined fluid flow rate through said tubing, and wherein said predetermined upline pressure maintained by said upline pressurization means varies as a function of the speed of rotation of said rotor.

16. A flow system as defined in claim 12 wherein said upline pressurization means comprise additional pressure means compressively engaged to the sidewall of said tubing for at least partially occluding the lument thereof, and additional drive means for advancing the point of engagement of said additional pressure means along an additional segment of said tubing.

17. A flow system as defined in claim 16 including pressure control means responsive to the pressure of said fluid in said tubing between said pressure means and said additional pressure means for varying the operation of said additional pressure means to maintain a predetermined pressure in said tubing.

18. A flow system as defined in claim 12 wherein said pressure members are disposed in equispaced relationship on the circumference of said rotor, and said pressure plate brings said tubing into engagement with said pressure member only over a segment of said tubing substantially corresponding to the spacing of said pressure members on the circumference of said rotor.

19. A flow system as defined in claim 12 wherein said downline pressurization means comprise a slidably mounted plunger spring-biased against the wall of said tubing.

20. A flow system as defined in claim 12 wherein said upline pressurization means comprise:
an additional plurality of pressure members, at all times at least one of said pressure members being in compressive engagement with the sidewall of said tubing so as to at least partially occlude the lumen thereof;
means including an additional pressure plate for bringing said tubing into compressive engagement with said one of said pressure members; and
additional drive means for rotatably driving said rotor whereby the lumen of said tubing is repetitively and progressively restored along an additional segment of said tubing to increase the pressure of said fluid upline of said point of engagement.

21. A flow system as defined in claim 20 wherein said pressure plates are formed as a single unit and mounted for reciprocative movement into and out of engagement with said pressure members.

22. A flow system as defined in claim 20 wherein said additional drive means comprise a rotational coupling between said rotors.

23. A flow system as defined in claims 20 including a stepper motor for driving said rotor of said upline pressurization means, and pressure control means responsive to the pressure in said tubing upline of the point of engagement of said pressure member of said metering means, and downline of the point of engagement of said pressure member of said upline pressurization means, for applying stepping pulses to said stepper motor at a rate which maintains a desired predetermined upline pressure level at said point of engagement.

24. A flow system as defined in claim 12 wherein said tubing is formed of vinyl.

25. In a metering apparatus for infusing a fluid from a supply reservoir to the human body through a length of flexible-walled tubing of the type exhibiting incomplete restoration upon repeated compressive cycling thereof, having, in combination:
- metering means continuously including at least one pressure means compressively engaged to the sidewall of the tubing for completely occluding the lumen thereof;
- drive means for advancing the point of engagement of said pressure means along a segment of the tubing, the lumen of the tubing being repetitively and progressively compressed and restored along said segment to urge fluid through the tubing;
- downline pressurization means for continuously at least partially restricting the lumen of the tubing downline of said tubing segment to increase the pressure of the fluid within said segment downline of said point of engagement; the improvement comprising:
- upline pressurization means operatively engaging said tubing for increasing the pressure of said fluid in said segment upline of said point of engagement, the increase in pressure of said fluid at said point of engagement assisting in post-compressive reformation of said tubing for improved metering accuracy.

26. Metering apparatus as defined in claim 25 including pressure control means responsive to the pressure in said tubing upline of said point of engagement for varying the operation of said upline pressurization means to maintain said upline pressures at a predetermined level.

27. Metering apparatus as defined in claim 26 wherein said pressure control means are also responsive to the rate of advance of said pressure means along said tubing segment.

28. Metering apparatus as defined in claim 27 wherein said drive means advance said pressure means to maintain a predetermined fluid flow rate through said tubing, and wherein said predetermined upline pressure maintained by said upline pressurization means varies as a function of said predetermined rate.

29. Metering apparatus as defined in claim 25 wherein said upline pressurization means comprise additional pressure means compressively engaged to the sidewall of said tubing for at least partially occluding the lumen thereof, and additional drive means for advancing the point of engagement of said additional pressure means along an additional segment of said tubing.

30. Metering apparatus as defined in claim 29 including pressure control means responsive to the pressure of said fluid in said tubing between said pressure means and said additional pressure means for varying the operation of said additional pressure means to maintain a predetermined pressure in said tubing.

31. Metering apparatus as defined in claim 30 wherein said pressure control means vary the rate of advance of said additional pressure means along said additional segment.

32. Metering apparatus as defined in claim 39 including pressure sensing means disposed along said tubing between said segment and said additional segment for providing a control signal indicative of the fluid pressure level in said tubing between said pressure means and said additional pressure means, said additional drive means being responsive to said control signal to vary the drive of said additional pressure means to maintain a predetermined pressure level at said sensing means.

33. Metering apparatus as defined in claim 32 wherein said control signal is applied to said additional drive means to vary the rate of advance of said additional pressure means along said additional segment.

34. Metering apparatus as defined in claim 25 wherein said tubing is formed of vinyl.

35. Metering apparatus as defined in claim 25 wherein said downline pressurization means comprise a slidably-mounted plunger spring-biased against the sidewall of said tubing.

36. In a metering apparatus for infusing a fluid from a supply reservoir to the human body through a length of flexible-walled tubing of the type exhibiting incomplete restoration upon repeated compressive cycling thereof; having:
- metering means including a rotor having along its circumference a plurality of pressure members, at all times at least one of said pressure members being in compressive engagement with the sidewall of the tubing and completely occluding the lumen thereof;
- means including a pressure plate for bringing the tubing into compressive engagement with said one of said pressure members along a segment of said tubing;
- drive means for rotatably driving said rotor whereby the lumen of the tubing is repetitively and progressively compressed and restored along said segment to urge fluid through the tubing;
- downline pressurization means for continuously at least partially restricting the lumen of the tubing downline of said tubing segment to increase the pressure of the fluid within said segment to increase the pressure of the fluid within said segment downline of point of engagement of said pressure member; the improvement comprising:
- upline pressurization means operatively engaging said tubing for increasing the pressure of said fluid in said segment upline of said point of engagement, the increase in pressure of said fluid at said point of engagement assisting in post-compressive reformation of said tubing for improved metering accuracy.

37. Metering apparatus as defined in claim 36 including pressure control means responsive to the pressure in said tubing upline of said point of engagement for varying the operation of said upline pressurization means to maintain said upline pressures at a predetermined level.

38. Metering apparatus as defined in claim 37 wherein said pressure control means are also responsive to the rate of advance of said pressure means along said tubing segment.

39. Metering apparatus as defined in claim 38 wherein said drive means rotate said rotor to maintain a predetermined fluid flow rate through said tubing, and wherein said predetermined upline pressure maintained by said upline pressurization means varies as a function of the speed of rotation of said rotor.

40. Metering apparatus as defined in claim 36 wherein said upline pressurization means comprise additional pressure means compressively engaged to the sidewall of said tubing for at least partially occluding the lumen thereof, and additional drive means for advancing the point of engagement of said additional pressure means along an additional segment of said tubing.

41. Metering apparatus as defined in claim 40 including pressure control means responsive to the pressure of said fluid in said tubing between said pressure means and said additional pressure means for varying the operation of said additional pressure means to maintain a predetermined pressure in said tubing.

42. Metering apparatus as defined in claim 36 wherein said pressure members are disposed in equispaced relationship on the circumference of said rotor, and said pressure plate brings said tubing into engagement with said pressure member only over a segment of said tubing substantially corresponding to the spacing of said pressure members on the circumference of said rotor.

43. Metering apparatus as defined in claim 36 wherein said downline pressurization means comprise a slidably-mounted plunger spring-biased against the wall of said tubing.

44. Metering apparatus as defined in claim 36 wherein said upline pressurization means comprise:
an additional plurality of pressure members, at all times at least one of said pressure members being in compressive engagement with the sidewall of said tubing so as to at least partially occlude the lumen thereof;
means including an additional pressure plate for bringing said tubing into compressive engagement with said one of said pressure members; and
additional drive means for rotatably driving said rotor whereby the lumen of said tubing is repetitively and progressively restored along an additional segment of said tubing to increase the pressure of said fluid upline of said point of engagement.

45. Metering apparatus as defined in claim 44 wherein said pressure plates are formed as a single unit and mounted for reciprocative movement into and out of engagement with said pressure members.

46. Metering apparatus as defined in claim 44 wherein said additional drive means comprise a rotational coupling between said rotors.

47. Metering apparatus as defined in claim 44 including a stepper motor for driving said rotor of said upline pressurization means, and pressure control means responsive to the pressure in said tubing upline of the point of engagement of said pressure member of said metering means, and downline of the point of engagement of said pressure member of said upline pressurization means, for applying stepping pulses to said stepper motor at a rate which maintains a desired predetermined upline pressure level at said point of engagement.

48. Metering apparatus as defined in claim 36 wherein said tubing is formed of vinyl.

49. In a metering apparatus for infusing a fluid from a supply reservoir to the human body through a length of flexible-walled tubing of the type exhibiting incomplete restoration upon repeated compressive cycling thereof, having, in combination:
metering means including a rotor having in equispaced relationship along its circumference a plurality of pressure members, at all times at least one of said pressure members being in compressive engagement with the sidewall of said tubing and completely occluding the lumen thereof;
means including a pressure plate for bringing said tubing into compressive engagement with said one of said pressure members only over a segment of said tubing substantially corresponding to the spacing of said pressure members on the circumference of said rotor;
drive means for rotatably driving said rotor whereby the lumen of said tubing is repetitively and progressively compressed and restored along said segment to urge fluid through said tubing;
downline pressurization means comprising a movable plunger spring-biased against the wall of said tubing, for continuously at least partially restricting the lumen of said tubing downline of said tubing segment to increase the pressure of the fluid within said segment downline of said point of engagement of said pressure member; the improvement comprising:
upline pressurization means comprising a rotor having along its circumference a plurality of pressure members, at all times at least one of said pressure members being in compressive engagement with the sidewall of said tubing and at least partially occluding the lumen thereof;
means including an additional pressure plate for bringing said tubing into compressive engagement with said one of said pressure members of said upline pressurization means;
additional drive means for rotatably driving said rotor whereby the lumen of said tubing is repetitively and progressively compressed and restored to urge fluid through said tubing; and
pressure control means responsive to the pressure of said fluid upline of said point of engagement of said pressure members of said metering means for varying the speed of rotation of said additional rotor to maintain said upline pressure at a predetermined level for improved metering accuracy.

50. The method of infusing a fluid from a supply reservoir into the human body, comprising the steps of:
establishing a flow path between the supply reservoir and the human body through a length of flexible-walled tubing of the type exhibiting incomplete restoration upon repeated compressive cycling thereof;
continuously compressing the sidewall of said tubing so as to completely occlude said tubing;
repetitively advancing the point of compression of said tubing along a segment thereof whereby the lumen of said tubing is repetitively and progressively compressed and restored along said segment to urge fluid through said tubing; and
increasing the pressure of the fluid within said segment upline of said point of compression to assist in reformation of said tubing segment for improved metering accuracy.

51. The method of infusing a fluid defined in claim 50 comprising the additional step of at least partially restricting the lumen of said tubing downline of said tubing segment to increase the pressure of the fluid within said segment both upline and downline of said point of compression.

52. The method of infusing fluid as defined in claim 50 wherein the flow path is established through flexible-walled vinyl tubing.

* * * * *